United States Patent [19]
Cotrel

[11] Patent Number: 5,651,789
[45] Date of Patent: *Jul. 29, 1997

[54] TRANSVERSE FIXATION DEVICE FOR ENSURING A RIGID TRANSVERSE CONNECTION BETWEEN TWO RODS OF A SPINAL OSTEOSYNTHESIS SYSTEM

[75] Inventor: Yves Paul Cotrel, Paris, France

[73] Assignee: Sofamor Danek Group, Memphis, Tenn.

[*] Notice: The term of this patent shall not extend beyond the expiration date of Pat. No. 5,487,742.

[21] Appl. No.: 478,897

[22] Filed: Jun. 7, 1995

Related U.S. Application Data

[63] Continuation of Ser. No. 158,156, Nov. 24, 1993, Pat. No. 5,487,742, which is a continuation of Ser. No. 666,665, Mar. 7, 1991.

[51] Int. Cl.⁶ .................................................. A61F 5/01
[52] U.S. Cl. ............................................ 606/61; 623/17
[58] Field of Search .............................. 623/17, 18; 606/53, 606/54, 60, 61

[56] References Cited

U.S. PATENT DOCUMENTS

| | | | |
|---|---|---|---|
| 2,187,642 | 1/1940 | Brown . | |
| 2,439,995 | 4/1948 | Thrailkill | 606/60 |
| 2,497,626 | 2/1950 | Persall | 606/54 |
| 4,271,832 | 6/1981 | Evans et al. | 606/54 |
| 4,628,922 | 12/1986 | Dewar | 606/54 |
| 4,641,636 | 2/1987 | Cotrel | 606/481 |
| 4,815,453 | 3/1989 | Cotrel | 128/500 |
| 5,002,542 | 3/1991 | Frigg | 606/61 |
| 5,102,412 | 4/1992 | Rogozinski | 606/61 |
| 5,122,131 | 6/1992 | Tsou | 606/53 |
| 5,176,678 | 1/1993 | Tsou | 606/54 |
| 5,334,203 | 8/1994 | Wagner | 606/53 |
| 5,342,360 | 8/1994 | Faccioli et al. | 606/53 |
| 5,344,422 | 9/1994 | Frigg | 606/60 |
| 5,382,248 | 1/1995 | Jacobson et al. | 606/60 |

FOREIGN PATENT DOCUMENTS

| | | | |
|---|---|---|---|
| 0348272 | 12/1989 | European Pat. Off. . | |
| 2244446 | 2/1975 | France . | |
| 2642642 | 8/1990 | France | 606/61 |
| 653799 | 6/1937 | Germany . | |

*Primary Examiner*—David Isabella
*Attorney, Agent, or Firm*—Woodard, Emhardt, Naughton, Moriarty & McNett

[57] ABSTRACT

This device comprises two fixation elements (4), each consisting of a hook (4) designed so as to be able to cover a rigid transverse bar (3) in a sliding manner and equipped with means (9, 8) for locking on the bar (3); this hook is made up of a body (5) and at least one blade. This device forms a relatively simple transverse connection device which can be positioned quickly and which has great torsional and flexural strength.

36 Claims, 3 Drawing Sheets

Fig. 1
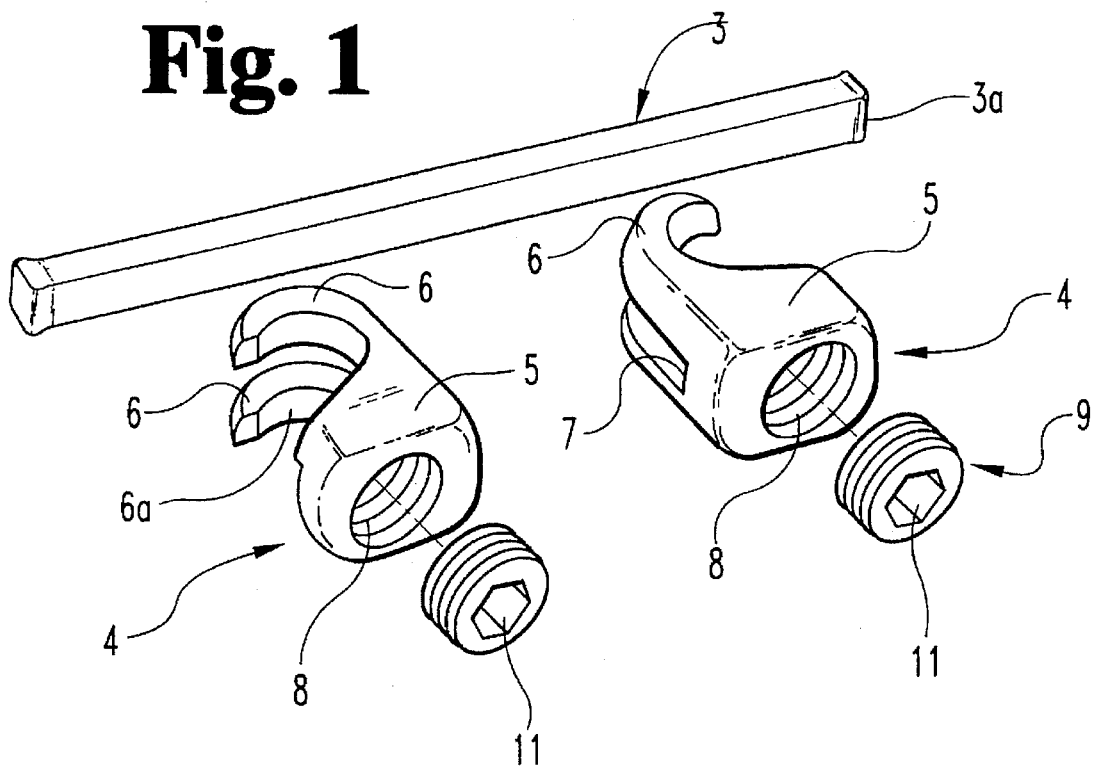
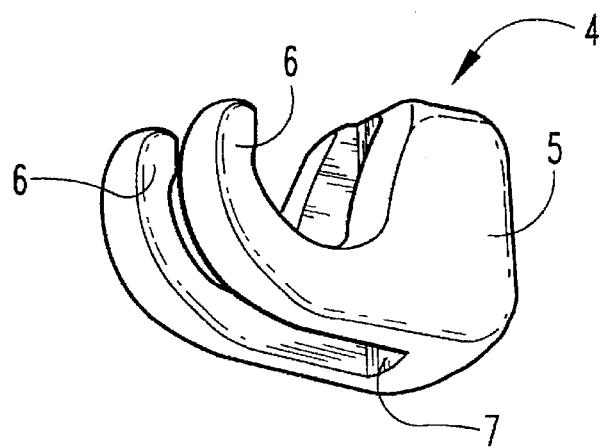
Fig. 2

TRANSVERSE FIXATION DEVICE FOR ENSURING A RIGID TRANSVERSE CONNECTION BETWEEN TWO RODS OF A SPINAL OSTEOSYNTHESIS SYSTEM

This application is a continuation of parent application Ser. No. 08/158,156, filed Nov. 24, 1993, now U.S. Pat. No. 5,487,742, issued on Jan. 30, 1996, which is a file-wrapper continuation of Ser. No. 08/666,665, filed Mar. 7, 1991.

The present invention relates to a fixation element for a transverse fixation device designed to ensure a rigid connection between two rods of a spinal osteosynthesis system, and to the transverse fixation device equipped with these elements.

It is known that in spinal osteosynthesis using the COTREL-DUBOUSSET technique, use is made of a transverse connection device (known by the abbreviation DTT) consisting of a fixed hook provided with a threaded rod, and of three free hooks which make it possible to bring together or space apart two knurled rods, by means of nuts and screws.

This system, necessary in order to guarantee the stability of the osteosynthesis equipment in the form of a frame, has the following disadvantages:
- the time needed for its positioning is relatively long,
- its positioning is quite difficult,
- its torsional and flexural strength is relatively low.

The aim of the invention is therefore to overcome these disadvantages.

According to the invention, the fixation element consists of a hook designed so as to be able to cover, in a sliding manner, a rigid transverse bar and equipped with means for locking on said bar. This hook is made up of a body and two blades which are spaced apart by a distance of a width corresponding to that of the bar. A span for the hook to bear on the bar is made on the body between the blades, which blades extend on each side of the bar when the hook straddles the latter.

According to one feature of the invention, the two blades are curved in a radius of curvature corresponding to that of the rods, and thus designed so as to enclose the latter.

According to another characteristic, the span is planar in order to be able to bear on a planar surface of a bar of rectangular cross-section, the two blades extending parallel to one another on both sides of the said span.

The transverse fixation device, to which the invention also relates, comprises in combination a rigid bar of suitable length, and a pair of elements for fixation of the bar on the rods, such as mentioned hereinabove, being capable of being fixed in an adjustable manner at a chosen position on the bar.

This equipment is simplified compared to the equipment previously used and can therefore be positioned by the surgeon more quickly and more simply. In addition, it has a much greater torsional and flexural strength on account of the bar whose cross-section is considerable and constant over its entire length.

The invention will now be described with reference to the attached drawings which illustrate an embodiment thereof by way of a non-limiting example.

FIG. 1 is an exploded perspective view of an embodiment of the transverse fixation device according to the invention.

FIG. 2 is a perspective view, on an enlarged scale compared to FIG. 1, of one of the fixation elements of the device.

Figure 6:
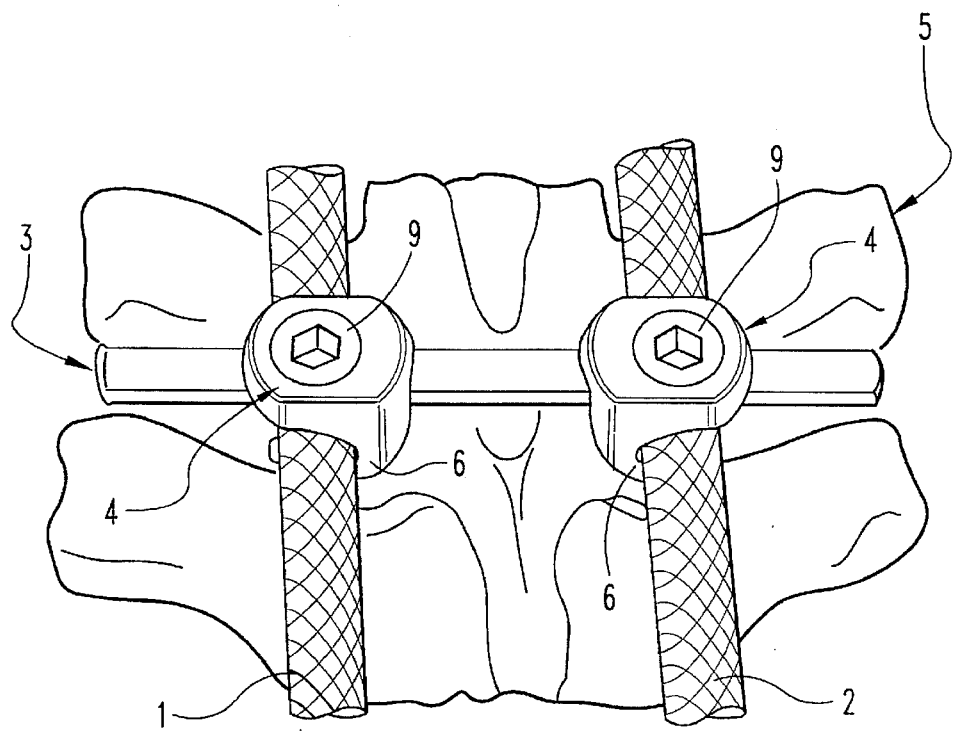
FIG. 6 is a perspective view of the transverse connection device according to FIGS. 1 to 5, positioned on a spinal segment.

The drawings show a transverse fixation device designed to ensure a rigid transverse connection between two rods 1 and 2 of a spinal osteosynthesis system which is to be positioned on a spinal segment S, which is shown partially in FIG. 6.

This device comprises, on the one hand, a rigid bar 3, cut to a suitable length, slightly greater than the space between the two rods 1 and 2, and a pair of fixation elements 4 which can be fixed in an adjustable manner at a chosen position on the bar 3. The latter has a suitable cross-section, for example rectangular.

Figure 3:
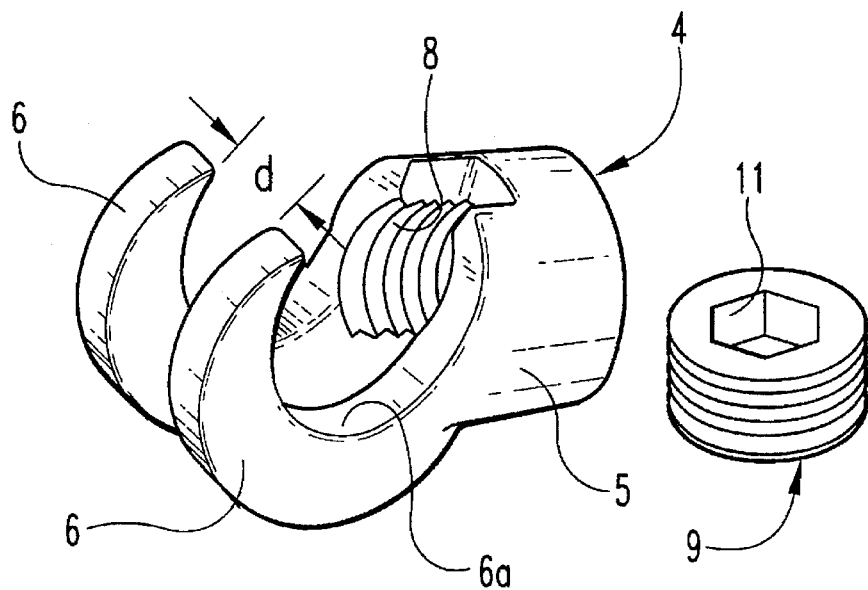
FIG. 3 is an exploded perspective view, at a different angle from FIGS. 1 and 2, of one of the hooks of the device, and of its plug for locking on the rod enclosed by this hook.
Figure 4:
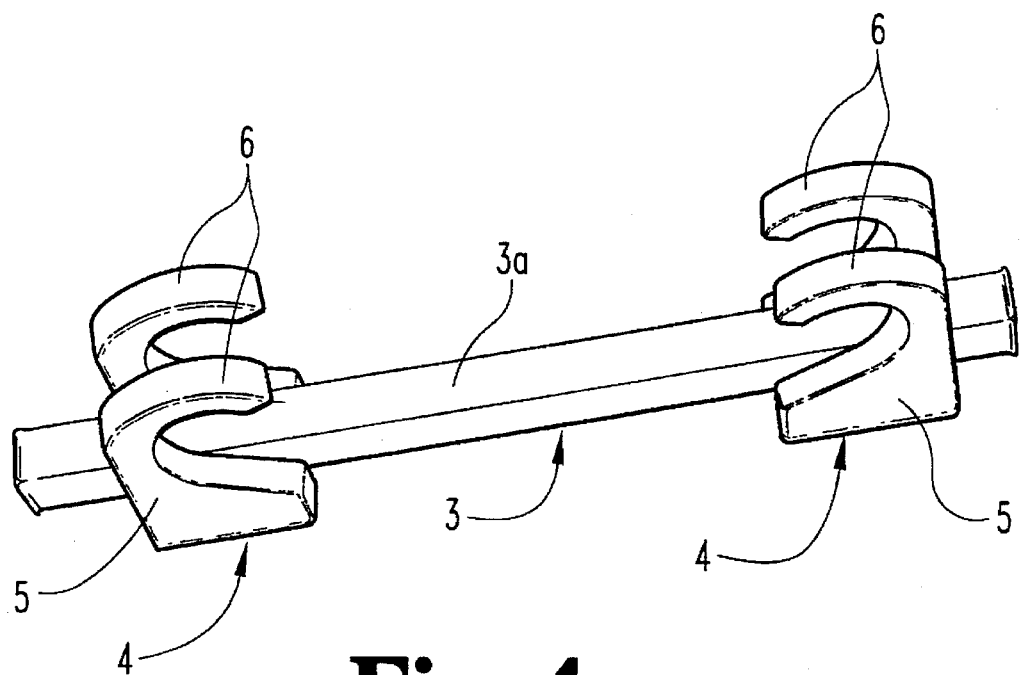
FIG. 4 is a perspective view of the device in FIGS. 1 to 3 when assembled, viewed from under the hooks, from the direction of the rods of the device.
Figure 5:
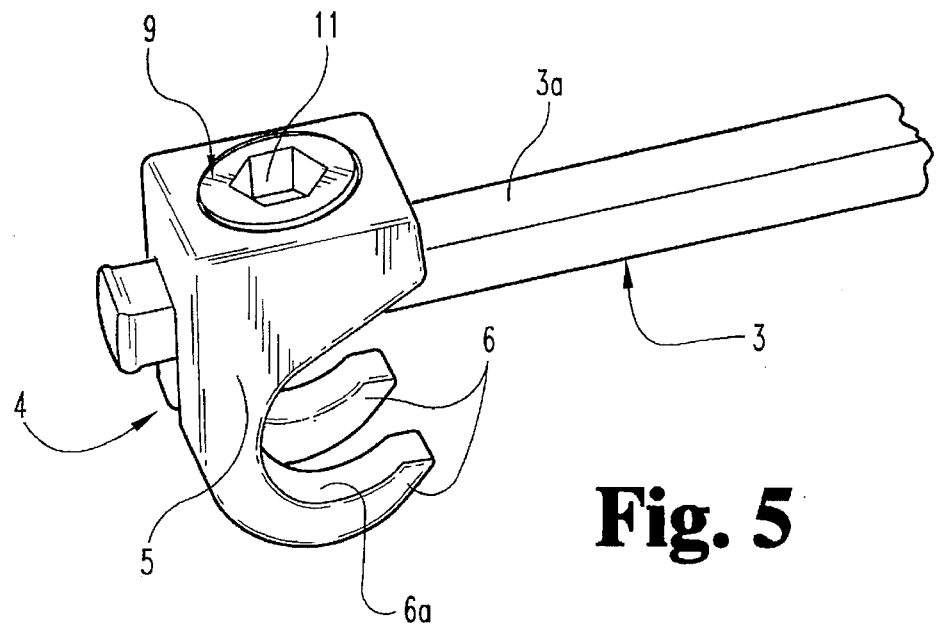
FIG. 5 is a partial elevation view of the bar of the device in FIGS. 1 to 4 straddled by a hook.

Each element 4 consists of a hook designed so as to be able to cover the bar 3 in a sliding manner. To this end, each hook 4 comprises a body 5 and two blades 6 extending parallel to one another and separated by a distance d (FIG. 3) whose width corresponds to that of one of the surfaces 3a of the bar 3 of rectangular cross-section, in order to be able to straddle the bar by extending on both sides of the latter. The two blades 6 are curved in a radius of curvature corresponding to that of the knurled rods 1 and 2, in order to be able to enclose the latter in their bearing surfaces 6a, for example over slightly more than a half circumference.

Formed between the base of the two blades 6 and on the body 5 is a span 7 for the bearing of a surface 3a of the bar 3, this span 7 constituting the base of the seat of the bar in the hook 4. The span 7 extends from one end of the body 5 to the other, and in its central zone it is interrupted by a tapped hole 8 (FIGS. 1 and 3) formed in the body 5. A threaded plug 9 is designed to be able to be screwed into the corresponding tapped hole 8, in such a way that, at the end of screwing, it comes to bear on the surface 3a of the bar 3 placed in abutment on the span 7 and to lock the bar 3 by means of clamping between the plug 9 and the rod 1 (or 2). The surface for the bearing of the plug 9 on the bar 3 is planar or may optionally be provided with catching means, such as a point. In each plug 9, a profiled orifice 11 is made, for example a hexagonal socket, designed to receive a tool (not shown) for screwing of the plug 9.

In order to position the device which has just been described, the surgeon places the bar 3 on the rods 1, 2 and then fits the two hooks 4 by making them straddle the bar 3 in order to enclose the rods 1, 2. Depending on the assembly chosen, the hooks 4 are placed either for spacing the rods 1 and 2 (FIG. 6), or for bringing together these rods. In the spacing position, the blades 6 are oriented in opposite directions to one another, their base being situated between the rods 1 and 2. In contrast, in the position of bringing together, the hooks 4 are placed in such a way that their blades 6 are oriented towards one another, their base being situated to the outside of the rods 1 and 2.

The fixation of the bar 3 on the rods 1 and 2 is therefore carried out after the surgeon has spaced apart or brought together the two hooks 4, the center distance being maintained by tightening the screws or plugs 9 for locking the hooks 4 in their chosen position on the bar 3. The latter is then fixed relative to the two rods 1 and 2 and ensures the cohesion or stability of the osteosynthesis system, with great torsional and flexural strength.

The invention is not limited to the embodiment described and can comprise alternative embodiments. Thus, if desired, the cross-section of the bar 3 could be other than rectangular, and the plugs or screws 9 for locking of the hooks 4 can be replaced by any equivalent means.

I claim:

1. A spinal osteosynthesis system, comprising:

a pair of spinal rods configured to be implanted adjacent a spinal segment;

a transverse bar configured to be implanted adjacent a spinal segment; and a pair of transverse fixation devices for connecting said transverse bar to each of said spinal rods, each of said fixation devices including a body and a hook portion, said hook portion including a hook-shaped blade extending outwardly from said body and defining a first bearing surface for engaging one of said rods, said first surface configured to conform to a portion of an outer surface of said one of said rods, and said body defining a second bearing surface configured to abut a portion of said bar when said bar is transverse to one of said rods.

2. The spinal osteosynthesis system according to claim 1 wherein said hook-shaped blade curves in a radius of curvature corresponding to that of the rods, and thus to enclose one of said rods when one of said rods is fully seated within the hook-shaped blade.

3. The spinal osteosynthesis system according to claim 2, wherein the bar has a rectangular cross-section and said second surface is planar.

4. The system according to claim 1 wherein said rods are knurled.

5. The system according to claim 1, further comprising a locking means for providing a rigid connection between said transverse bar and said rods, said locking means including:

a hole defined through said body of each said fixation device, said hole intersecting said second bearing surface of said body; and a plug configured for engagement in said hole, said plug having a head portion at one end and a tip portion at an opposite end, whereby when said bar is engaged to said second bearing surface and said rod is engaged to said first bearing surface, said plug is extendable into said hole until said tip portion of said plug contacts said bar and presses said bar against the rod, thereby locking said rod and said transverse bar together.

6. The spinal osteosynthesis system according to claim 5, wherein said head portion of said plug defines an orifice profiled to receive a screwing tool.

7. The system according to claim 6 wherein said orifice is hexagonal shaped.

8. The system according to claim 5, wherein said head portion and said tip portion of said plug have the same cross-sectional diameter.

9. The system according to claim 5, wherein said plug further includes catching means for engaging said bar.

10. The system according to claim 9 wherein said catching means includes a point extending from said tip of said plug.

11. The system according to claim 5 wherein said plug defines external threads and said hole defines internal threads, said external threads mating with internal threads defined in said hole.

12. The system according to claim 11, wherein said plug is threaded along its entire length including said head portion of said plug.

13. A transverse fixation device for connecting a first elongate member to a second elongate member of a spinal osteosynthesis system, comprising:

a body and a hook portion attached to said body;

said hook portion including a hook-shaped blade extending outwardly from said body and defining a first bearing surface for engaging the first elongate member, said first surface configured to conform to a portion of an outer surface of the first elongate member; and said body defining a second bearing surface transverse to said first bearing surface configured to abut a portion of the second elongate member when the second elongate member is transverse to the first elongate member.

14. The transverse fixation device according to claim 13, wherein said outwardly extending hook-shaped blade curves in a radius corresponding to a radius of the first elongate member to slidingly enclose the first elongate member when the first elongate member is fully seated within said blade.

15. The transverse fixation device according to claim 14 wherein the first elongate member is a spinal rod and the second elongate member is a transverse bar.

16. The transverse fixation device according to claim 13, wherein the portion of the outer surface of the second elongate member is planar and said second bearing surface is planar.

17. The transverse fixation device according to claim 13, further comprising:

a hole defined in said body and opening at said second bearing surface; and a plug engageable within said hole to extend through said opening and bear against the second elongate member to clamp the second elongate member against the first elongate member when the first elongate member is engaged to said first bearing surface and the second elongate member is transverse to the first elongate member.

18. The transverse fixation device according to claim 17, wherein said head portion of said plug defines an orifice profiled for receiving a screwing tool.

19. The transverse fixation device according to claim 18 wherein said orifice is hexagonal shaped.

20. The transverse fixation device according to claim 17, wherein said head portion and said tip portion of said plug have the same cross-sectional diameter.

21. The transverse fixation device according to claim 17, wherein said plug further includes catching means for engaging the second elongate member.

22. The transverse fixation device according to claim 21 wherein said catching means includes a point extending from said tip of said plug, said point configured to contact the second elongate member.

23. The transverse fixation device according to claim 17 wherein said plug defines external threads and said hole defines internal threads, said external threads mating with internal threads defined in said hole.

24. The transverse fixation device according to claim 23, wherein said plug is threaded along its entire length including said head portion of said plug.

25. A spinal osteosynthesis system, comprising:

a spinal rod configured to be implanted adjacent a spinal segment;

a transverse bar configured to be implanted adjacent a spinal segment; and a fixation element for insuring a rigid transverse connection between said rod and said bar, said fixation element including a body and a hook portion attached to said body, said hook portion defining a hook-shaped blade extending outwardly from said body and defining a first bearing surface for engaging said rod, and said body defining a second bearing surface transverse to said first bearing surface configured to bear on a portion of said bar.

26. The system according to claim 25, wherein said outwardly extending hook-shaped blade curves in a radius corresponding to the radius of said spinal rod to slidingly enclose said rod when it is fully seated within said blade.

27. The system according to claim 26 wherein said rod is knurled.

28. The system according to claim 25, wherein the portion of the outer surface of said transverse bar is planar and said second surface is planar.

29. The system according to claim 25, further comprising a locking means for providing a rigid connection between said rod and said bar, said locking means including:

a hole defined through said body, said hole extending from said second bearing surface of said body to an opposite surface of said body; and a plug having a head portion at one end and a tip portion at an opposite end, said plug configured for engagement in said hole so that when said bar is engaged to said second bearing surface and when said rod is engaged to said first bearing surface said plug may be placed into said hole until said tip portion of said plug contacts said bar and presses said bar firmly against said rod to lock said rod and said transverse bar together in position.

30. The system according to claim 29, wherein said head portion of said plug defines an orifice profiled for receiving a screwing tool.

31. The system according to claim 30 wherein said orifice is hexagonal shaped.

32. The system according to claim 29, wherein said head portion and said tip portion of said plug have the same cross-sectional diameter.

33. The system according to claim 29 wherein said plug defines external threads and said hole defines internal threads, said external threads mating with said internal threads defined in said hole.

34. The system according to claim 33, wherein said plug is threaded along its entire length including said head portion of said plug.

35. The system according to claim 29, wherein said plug further includes catching means for engaging said bar.

36. The system according to claim 35 wherein said catching means includes a point extending from said tip of said plug.

* * * * *

UNITED STATES PATENT AND TRADEMARK OFFICE
CERTIFICATE OF CORRECTION

PATENT NO. : 5,651,789
DATED : July 29, 1997
INVENTOR(S) : Yves Paul Cotrel

It is certified that error appears in the above-identified patent and that said Letters Patent is hereby corrected as shown below:

On the title page, left column, immediately preceding

"[51] Int. Cl. 6 .....................A61F 5/01"

insert the following:

--[30]   Foreign Application Priority Data
   Mar. 8, 1990 [FR]  France ................90 02970--

Signed and Sealed this

First Day of September, 1998

Attest:

BRUCE LEHMAN

Attesting Officer

Commissioner of Patents and Trademarks